United States Patent
Kabus et al.

(10) Patent No.: US 9,414,773 B2
(45) Date of Patent: Aug. 16, 2016

(54) RESPIRATORY MOTION DETERMINATION APPARATUS

(75) Inventors: Sven Kabus, Hamburg (DE); Hans-Aloys Wischmann, Henstedt-Ulzburg (DE); Cristian Lorenz, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 147 days.

(21) Appl. No.: 14/125,182

(22) PCT Filed: Jun. 19, 2012

(86) PCT No.: PCT/IB2012/053075
§ 371 (c)(1),
(2), (4) Date: Dec. 10, 2013

(87) PCT Pub. No.: WO2012/176114
PCT Pub. Date: Dec. 27, 2012

(65) Prior Publication Data
US 2014/0133717 A1    May 15, 2014

(30) Foreign Application Priority Data

Jun. 21, 2011  (EP) .................................... 11305777

(51) Int. Cl.
*G06K 9/00* (2006.01)
*A61B 5/11* (2006.01)
*A61B 6/00* (2006.01)
*A61B 6/03* (2006.01)
(Continued)

(52) U.S. Cl.
CPC ............... *A61B 5/1128* (2013.01); *A61B 5/113* (2013.01); *A61B 6/037* (2013.01); *A61B 6/5264* (2013.01); *A61B 6/5288* (2013.01); *G06T 7/0012* (2013.01); *G06T 7/0016* (2013.01); *G06T 7/20* (2013.01); *G06T 7/2033* (2013.01); *A61B 5/0456* (2013.01); *A61B 5/055* (2013.01); *A61B 5/7207* (2013.01); *A61B 2576/023* (2013.01); *G06T 2207/10076* (2013.01); *G06T 2207/30061* (2013.01)

(58) Field of Classification Search
USPC ......................................... 382/103, 128–134
See application file for complete search history.

(56) References Cited

U.S. PATENT DOCUMENTS 5,287,276 A    2/1994  Crawford et al.
8,285,359 B2   10/2012 Salla et al.
(Continued)

FOREIGN PATENT DOCUMENTS

| CN | 101702232 A | 10/2009 |
| CN | 101658426 A | 3/2010 |
| WO | 2011070465 A2 | 6/2011 |

*Primary Examiner* — Alex Liew (57) ABSTRACT

A respiratory motion determination apparatus determines respiratory motion of a living being (3). A raw data providing unit (2) provides raw data assigned to different times, wherein the raw data are indicative of a structure like the apex of the heart muscle, which is influenced by cardiac motion and by respiratory motion. A reconstruction unit (6) reconstructs intermediate images of the structure from the provided raw data. A structure detection unit (7) detects the structure in the reconstructed intermediate images. A respiratory motion determination unit (10) determines the respiratory motion of the living being based on the structure detected in the reconstructed intermediate images. This allows determining respiratory motion with high accuracy, without relying on, for example, a stable correlation between a tracking signal of an external respiratory gating device and respiratory phases.

18 Claims, 3 Drawing Sheets

(51) Int. Cl.
*G06T 7/00* (2006.01)
*G06T 7/20* (2006.01)
*A61B 5/113* (2006.01)
*A61B 5/00* (2006.01)
*A61B 5/0456* (2006.01)
*A61B 5/055* (2006.01)

(56) References Cited

U.S. PATENT DOCUMENTS

| | | | |
|---|---|---|---|
| 2001/0012385 A1* | 8/2001 | Hossack et al. | 382/128 |
| 2003/0190064 A1* | 10/2003 | Inoue | 382/128 |
| 2005/0123183 A1* | 6/2005 | Schleyer | G06T 5/20 382/131 |
| 2006/0140482 A1 | 6/2006 | Koehler | |
| 2008/0226149 A1* | 9/2008 | Wischmann et al. | 382/131 |
| 2008/0240536 A1 | 10/2008 | Soubelet et al. | |
| 2008/0273785 A1 | 11/2008 | Kesner | |
| 2008/0304730 A1* | 12/2008 | Abe | 382/131 |
| 2009/0060306 A1* | 3/2009 | Ohuchi et al. | 382/131 |
| 2009/0219301 A1* | 9/2009 | Gerard et al. | 345/643 |
| 2010/0049038 A1* | 2/2010 | Florent et al. | 600/425 |
| 2010/0081917 A1* | 4/2010 | Zhang | A61B 6/5217 600/407 |
| 2010/0150423 A1* | 6/2010 | Hong | G06K 9/0014 382/133 |
| 2012/0051515 A1* | 3/2012 | Brown | G06T 7/2033 378/65 |
| 2012/0201428 A1 | 8/2012 | Joshi et al. | |
| 2012/0237097 A1* | 9/2012 | Koehler et al. | 382/128 |

* cited by examiner

RESPIRATORY MOTION DETERMINATION APPARATUS

FIELD OF THE INVENTION

The invention relates to a respiratory motion determination apparatus, a respiratory motion determination method and a corresponding computer program for determining respiratory motion of a living being.

BACKGROUND OF THE INVENTION

Known combined positron emission tomography (PET) and computed tomography (CT) systems generate a CT image, which is used together with acquired PET raw data for reconstructing an attenuation corrected (AC) PET image. However, respiratory motion can lead to a blurring in the reconstructed AC PET image and to an incorrect attenuation correction, thereby reducing the quality of the reconstructed AC PET image. In order to reduce these adverse effects on image quality a motion compensation technique can be used, which splits the breathing cycle into a predetermined, small number of respiratory phases, using an external respiratory gating device like a respiratory belt for tracking the respiratory phase. The quality of the motion compensation technique relies on a stable correlation between the tracking signal generated by the external gating device and the respiratory phase, which is very difficult to achieve. The correlation between the tracking signal and the respiratory phase has therefore often a relatively low accuracy, which reduces the quality of determining respiratory phases and, thus, the quality of reconstructing a PET image based on the determined respiratory phases.

SUMMARY OF THE INVENTION

It is regarded as being an object of the present invention to provide a respiratory motion determination apparatus, a respiratory motion determination method and a computer program for determining respiratory motion of a living being, which allow providing an improved respiratory motion compensation.

In a first aspect of the present invention a respiratory motion determination apparatus for determining respiratory motion of a living being is presented, wherein the respiratory motion determination apparatus comprises:

a raw data providing unit for providing raw data assigned to different times, wherein the raw data are indicative of a structure, which is influenced by cardiac motion and by respiratory motion of the living being and which is a structure of the living being, wherein the raw data are usable for reconstructing an image of the structure, a reconstruction unit for reconstructing intermediate images of the structure from the provided raw data, a structure detection unit for detecting the structure in the reconstructed intermediate images, a respiratory motion determination unit for determining the respiratory motion of the living being based on the structure detected in the reconstructed intermediate images.

Since the respiratory motion determination unit determines the respiratory motion of the living being based on the structure, which is influenced by cardiac motion and by respiratory motion and which is detected in the intermediate images, which have been reconstructed from the raw data assigned to different times, the respiratory motion can be determined, without relying on a stable correlation between a tracking signal of an external respiratory gating device and respiratory phases. This allows determining respiratory motion with high accuracy, which in turn allows improving a motion compensation technique for reconstructing a respiratory motion compensated image.

The structure is preferentially a structure of the heart.

The respiratory motion of the living being can be the respiratory motion of any part of the living being, i.e. the respiratory motion is the respiratory motion of at least a part of the living being. For example, the determined respiratory motion is the respiratory motion of the entire lung or of a part of the lung. The determined respiratory motion can also be the respiratory motion of the entire heart or the respiratory motion of the structure.

The raw data providing unit can be a raw data acquisition unit like a PET data acquisition unit, a single photon emission computed tomography (SPECT) data acquisition unit, a CT acquisition unit, a magnetic resonance (MR) acquisition unit, et cetera. However, the raw data providing unit can also be a storing unit, in which the raw data are stored already and from which the raw data can be retrieved for providing the same. Moreover, the raw data providing unit can also be a receiving unit for receiving the raw data via a wireless or wired data connection from, for example, an imaging modality, wherein the raw data providing unit can be adapted to provide the received raw data. The respiratory motion determination apparatus can therefore be, for example, a computer system comprising at least the raw data providing unit, the reconstruction unit, the structure detection unit and the respiratory motion determination unit, or the respiratory motion determination apparatus can be an imaging system, wherein the raw data providing unit can be a raw data acquisition unit.

The living being is a person or an animal.

In a preferred embodiment, the respiratory motion determination apparatus further comprises:

a cardiac signal providing unit for providing a cardiac signal at the different times to which the raw data are assigned, wherein the cardiac signal is indicative of heart cycles, a raw data grouping unit for grouping raw data of a same heart cycle in a group based on the provided cardiac signal, wherein the reconstruction unit is adapted to reconstruct an intermediate image for each group depending on the raw data of the respective group.

The intermediate image of a group can therefore be regarded as being an image comprising averaged information, wherein the average is performed over a single heart cycle. Thus, the resulting intermediate images are independent of cardiac phases, but still dependent on respiratory motion. The respiratory motion determination unit can therefore determine the respiratory motion of the living being independent of the heart beats, thereby further improving the quality of determining the respiratory motion.

It is further preferred that the raw data providing unit is adapted to provide nuclear raw data as the raw data. In particular, the raw data providing unit is adapted to provide PET data as the raw data. The cardiac signal providing unit is preferentially adapted to provide an electrocardiogram signal (ECG) as the cardiac signal. Thus, preferentially PET raw data are acquired, i.e. individual PET events/counts are acquired, and stored together with the different times, i.e. with their timestamps. In parallel, the ECG signal is stored and the temporal correlation between the timestamps of the acquired PET raw data and the ECG signal is established.

The heart cycles are preferably identified in the ECG signal by automatically determining QRS complexes from the ECG signal, wherein the determined QRS complexes are used to split the raw data into segments corresponding to the heart cycles by using, for example, the R peaks. Preferentially, a time segment, which corresponds to a heart cycle and which is used for grouping the raw data, is defined by an R-to-R segment of the ECG signal. The reconstruction unit uses then the raw data, in particular, the PET count/events within a time segment for reconstructing an intermediate image for this time segment, i.e. for a group of raw data, which have timestamps within the respective time segment.

It is also preferred that the structure detection unit is adapted to detect the heart muscle as the structure. In a preferred embodiment, the structure detection unit is adapted to detect the apex of the heart muscle as the structure. The heart muscle, in particular, the apex of the heart muscle, is generally well detectable in the intermediate images, thereby allowing a high quality detection of the structure, which is used for determining the respiratory motion. Particularly if the intermediate images are non-attenuation corrected (NAC) PET images, the heart muscle is clearly visible and of much greater intensity then, for example, lung or liver structures. Moreover, since the heart resides directly on top of the diaphragm, its motion is a direct measure of the respiratory motion. Using the heart muscle, in particular, the apex of the heart muscle, as a structure for determining the respiratory motion can therefore further improve the quality of determining the respiratory motion.

It is also preferred that the respiratory motion determination unit is adapted to determine the positions of the structure in the reconstructed intermediate images as the respiratory motion of the living being and to determine for each reconstructed intermediate image the respective respiratory phase of the living being depending on the positions of the structure detected in the reconstructed intermediate images.

It is further preferred that the respiratory motion determination apparatus comprises a respiratory phase image set providing unit for providing a respiratory phase image set of the living being, wherein the respiratory motion image set comprises for different respiratory phases different images of the structure, wherein the respiratory motion determination unit is adapted to determine the respiratory phase of a reconstructed intermediate image by comparing the position of the structure in the reconstructed intermediate image with the position of the structure in the respiratory phase image set. In particular, the respiratory phase determination unit is adapted to determine the respiratory phase of a reconstructed intermediate image by determining the image of the provided respiratory phase image set showing the structure with a smallest distance to the structure shown in the reconstructed intermediate image and by determining the respiratory phase of the determined image of the respiratory phase image set with the smallest distance as the respiratory phase of the reconstructed intermediate image.

The respiratory phase image set is preferentially a multi-phase CT image or a multi-phase MR image of the living being, wherein the respiratory phase image comprises several CT or MR images for different respiratory phases and wherein a respiratory phase is determined for an intermediate image, in particular, for an intermediate PET image, by determining the CT or MR image with shortest distance between the apex position in the respective intermediate image and the apex position in the respective CT or MR image, wherein the respiratory phase of the respective CT or MR image with the shortest distance is determined as the respiratory phase of the respective intermediate image.

In another embodiment, the respiratory motion determination apparatus comprises a respiratory motion model providing unit for providing a respiratory motion model of the living being, wherein the respiratory motion model provides for different respiratory phases different positions of the structure to be detected, wherein the respiratory motion determination unit is adapted to determine the respiratory phase of a reconstructed intermediate image by comparing the position of the structure in the reconstructed intermediate image with the position of the structure in the respiratory motion model. Preferentially, the respiratory motion model and the respective reconstructed intermediate image are aligned before determining the respiratory phase. For example, the respiratory motion model can also model anatomical features like the pleura, the apex of the lungs, the tips of the lungs, the diaphragm, et cetera, wherein these anatomical features can be used for aligning the respiratory motion model with the respective reconstructed intermediate image. This allows determining the respiratory phase for the different reconstructed intermediate images, without using a patient-specific respiratory phase image like a multi-phase CT image or a multi-phase MR image. For example, this motion model can be obtained from a mean or patient-group specific average of CT or MR images of the respiratory motion, or from a simple geometric model of the torso and the respiratory motion.

It is further preferred that the respiratory motion determination unit is adapted to fit a trajectory to the respiratory movement of the structure and to determine respiratory phases based on the fitted trajectory, thereby defining respiratory phases for the reconstructed intermediate images. This allows determining the respiratory phases just based on the reconstructed intermediate images, without needing, for example, a respiratory phase image like a multi-phase CT or MR image, or a respiratory motion model.

Preferentially, the reconstruction unit is further adapted to reconstruct an image of the living being based on the determined respiratory phases. In particular, the reconstruction unit can be adapted to reconstruct for different respiratory phases different respiratory phase images based on the raw data of the respective respiratory phase. A respiratory phase image can be determined directly from the raw data of the respective phase or by averaging the reconstructed intermediate images of the same respective respiratory phase.

Preferentially, the respiratory cycle is divided into a number of respiratory intervals defining a corresponding number of respiratory phases. For example, the respiratory cycle can be divided into ten respiratory intervals defining ten respiratory phases. The intermediate images, which correspond to the same respiratory interval, are regarded as having the same respiratory phase. Thus, preferentially for each of the respiratory intervals a respiratory phase image is reconstructed based on the image raw data, which correspond to the respective respiratory interval. In particular, reconstructed intermediate images, which correspond to the same respiratory interval, are averaged for producing a respiratory phase image for the respiratory interval, i.e. for the respiratory phase defined by the respiratory interval. The different respiratory intervals can have the same length, i.e. the respiratory phases can be equidistant, or the respiratory intervals can have different lengths, i.e. the respiratory phases may not be equidistant. In particular, the lengths of the respiratory intervals can be a posteriori defined based on the motion states of the structure from the reconstructed intermediate images. For example, from the reconstructed intermediate images, i.e. from the movement of the structure, the end inhale state and the end exhale state can be determined, wherein respiratory intervals, which are centered on the end inhale state and end exhale state, can be defined such that they have a larger length than respiratory intervals between these states.

It is also preferred that the raw data are nuclear raw data, wherein the reconstructed intermediate images are reconstructed nuclear images, wherein the respiratory motion determination apparatus further comprises a respiratory phase image set providing unit for providing a respiratory phase image set of the living being, wherein the respiratory phase image set comprises for different respiratory phases different attenuation images of the living being, and wherein the reconstruction unit is further adapted to attenuation-correct the different nuclear respiratory phase images based on the determined respiratory phases and the provided respiratory phase image set. The attenuation correction of the individual nuclear respiratory phase images improves the quality of these images.

In a further preferred embodiment, the raw data are nuclear raw data, wherein the reconstructed intermediate images are reconstructed nuclear images and wherein the respiratory motion determination apparatus comprises a) a respiratory motion model providing unit for providing a respiratory motion model of the living being, wherein the respiratory motion model provides for different respiratory phases different positions of the structure of the heart, and b) a static attenuation image providing unit for providing a static attenuation image, wherein the reconstruction unit is adapted to i) deform the static attenuation image in accordance with the provided respiratory motion model for producing different attenuation images for different respiratory phases, and ii) attenuation-correct each reconstructed intermediate image based on the attenuation image produced for the respiratory phase of the respective reconstructed intermediate image. This allows performing an attenuation correction, even if an attenuation image is not provided for each respiratory phase.

The provided static attenuation image can be a static attenuation image of the living being, which is or which is based on, for example, a CT image of the living, or the provided static attenuation image is not based on the specific actual living being, but, for instance, an average of attenuation images of different persons, wherein each of these attenuation images may be reconstructed from raw data corresponding to a certain respiratory phase or to an entire respiratory cycle.

It is also preferred that the reconstruction unit is adapted to register the different respiratory phase images and to average the registered respiratory phase images for producing a static image. Moreover, the respiratory motion determination apparatus can comprise an attenuation image providing unit for providing an attenuation image of the object, wherein the reconstruction unit is adapted to attenuation correct the static image based on the provided attenuation image. The provided attenuation image is preferentially a static attenuation image.

In a further embodiment, the reconstruction unit is adapted to reconstruct a respiratory motion compensated image from the raw data and the determined respiratory motion.

The reconstruction unit can be adapted to reconstruct the respiratory motion compensated image directly from the raw data or indirectly from the raw data, i.e. by using, for instance, intermediate motion state images, which can then be combined in accordance with the determined respiratory motion. For reconstructing the motion state images the raw data can be grouped into a number of groups, for example, into 10 groups, defining a number of motion states, wherein for each group a motion state image can be reconstructed based on the raw data of the respective group. The respiratory motion compensated image can, for example, be attenuation corrected by using a corresponding attenuation map.

In an embodiment, a respiratory motion model can be provided, which describes the respiratory motion of an entire thorax region of the living being depending on the determined respiratory motion of the structure, in particular, depending on the respiratory motion of the apex of the heart muscle. In particular, this respiratory motion model can define the displacements of different lung regions with respiratory motion. The respiratory motion of the entire thorax portion together with the raw data can then be used for reconstructing a respiration compensated image of at least a part of the thorax. In an embodiment, raw data corresponding to the same position of the structure and, thus, to the same respiratory motion state, can be used for reconstructing motion state images, which can then be combined in accordance with the respiratory motion model for reconstructing a motion compensated image. In another embodiment, the raw data can be corrected for respiratory motion by using the determined respiratory motion of the entire thorax, wherein then the motion corrected raw data can be reconstructed for generating a respiratory motion compensated image. For instance, if the raw data are PET data, each corresponding line-of-response can be shifted in accordance with the determined respiratory motion of the entire thorax.

In a further aspect of the present invention a respiratory motion determination method for determining respiratory motion of a living being is presented, wherein the respiratory motion determination method comprises:

providing raw data assigned to different times by a raw data providing unit, wherein the raw data are indicative of a structure, which is influenced by cardiac motion and by respiratory motion of the living being and which is a structure of the living being, wherein the raw data are usable for reconstructing an image of the structure, reconstructing intermediate images of the structure from the provided raw data by a reconstruction unit, detecting the structure in the reconstructed intermediate images by a structure detection unit, determining the respiratory motion of the living being based on the structure detected in the reconstructed intermediate images by a respiratory motion determination unit.

In a further aspect of the present invention a computer program for determining respiratory motion of a living being is presented, wherein the computer program comprises program code means for causing a respiratory motion determination apparatus to carry out the steps of the respiratory motion determination method, when the computer program is run on a computer controlling the respiratory motion determination apparatus.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF PREFERRED EMBODIMENTS

Figure 1:
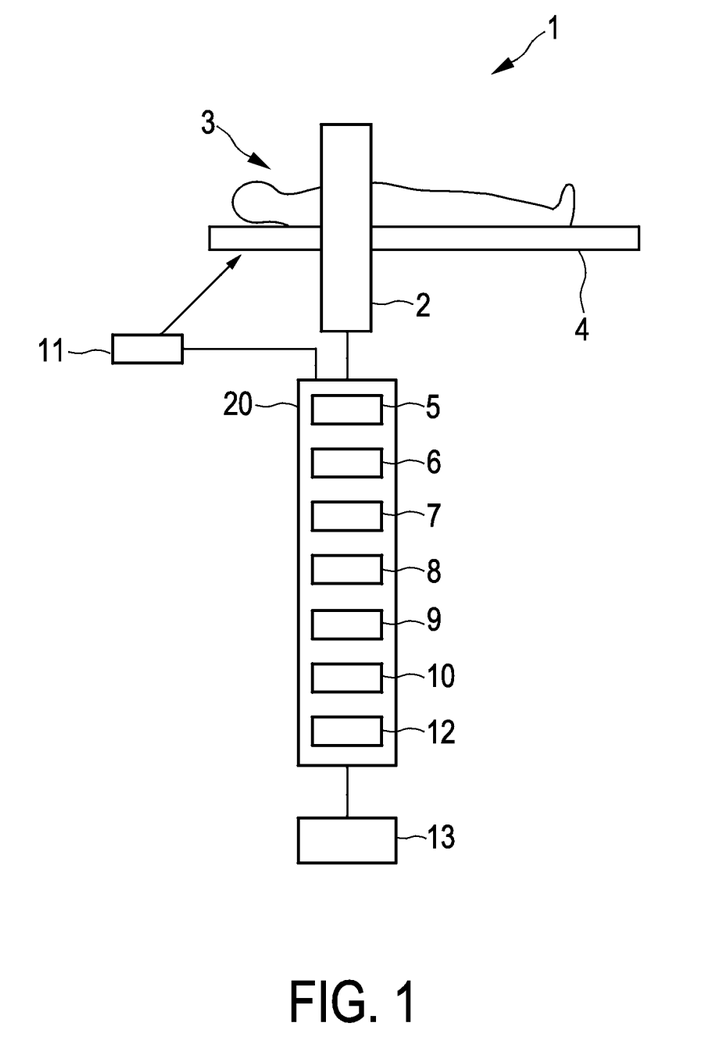
FIG. 1 shows schematically and exemplarily an embodiment of a respiratory motion determination apparatus for determining respiratory phases of a living being.

FIG. 1 shows schematically and exemplarily a respiratory motion determination apparatus for determining respiratory motion of a living being. In this embodiment, the respiratory phase determination apparatus 1 is a PET imaging system, which can be adapted to determine respiratory motion of a person 3 lying on a table 4 and to use the determined respiratory motion together with acquired PET raw data for reconstructing a PET image.

The respiratory motion determination apparatus 1 comprises a raw data providing unit 2 for providing raw data assigned to different times, wherein the raw data are indicative of a structure of the heart of the person 3 and usable for reconstructing an image of the structure of the heart, and wherein the structure of the heart is influenced by respiratory motion. In this embodiment, the raw data providing unit 2 is a PET raw data acquisition unit for acquiring PET raw data. The PET raw data are individual PET events or PET counts and are provided together with their respective acquisition times, i.e. with their timestamps. The respiratory motion determination apparatus further comprises a cardiac signal providing unit 11 for providing a cardiac signal at the different times to which the raw data are assigned, wherein the cardiac signal is indicative of heart cycles. The cardiac signal is preferentially an ECG signal, which is temporally correlated with the timestamps of the PET raw data.

The respiratory motion determination apparatus 1 further comprises a raw data grouping unit 5 for grouping raw data of a same heart cycle in a group based on the provided cardiac signal, wherein the reconstruction unit 6 is adapted to reconstruct an intermediate image for each group depending on the raw data of the respective group. In order to group the raw data such that raw data belonging to the same heart cycle are assigned to the same group, heart cycles can be identified in the ECG signal by automatically determining QRS complexes from the ECG signal.

Figure 2:
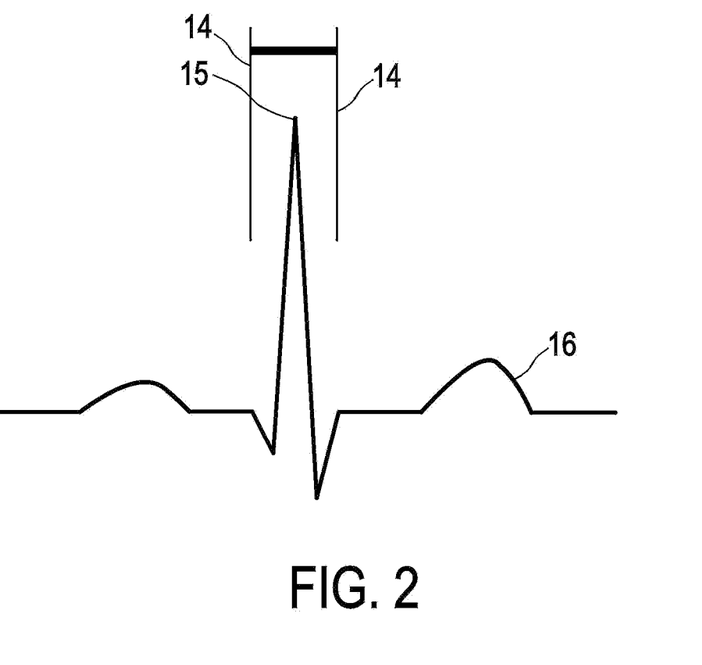
FIG. 2 shows schematically and exemplarily an ECG signal.

FIG. 2 shows schematically and exemplarily such an ECG signal 16 having a QRS complex between the lines 14. The QRS complex is usually the central and most visually obvious part the ECG signal 16. In particular, the QRS generally includes the R-peak 15 of the ECG signal 16. The raw data grouping unit 5 is preferentially adapted to split the raw data into segments corresponding to the heart cycles by using the R-peaks. Thus, preferentially a time segment, which corresponds to a heart cycle and which is used for grouping the raw data, is defined by an R-to-R segment of the ECG signal 16. All raw data belonging to the same R-to-R segment of the ECG signal 16 are preferentially grouped into a same group. The resulting intermediated images can be regarded as being a kind of average over a heart cycle such that the intermediated images are independent of cardiac phases, but still depending on respiratory phases.

The respiratory motion determination apparatus 1 further comprises a structure detection unit 7 for detecting the structure of the heart in the reconstructed intermediate images. In this embodiment, the structure detection unit 7 is adapted to detect the apex of the heart muscle as the structure of the heart.

Figure 3:
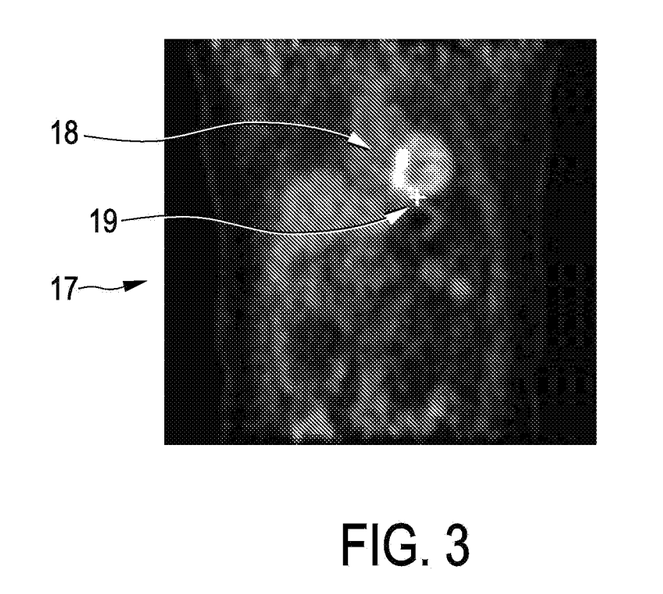
FIG. 3 shows schematically and exemplarily a PET image showing the heart and the apex of the heart muscle.

FIG. 3 shows schematically and exemplarily an intermediate image being a PET image 17 of the person 3. The heart muscle 18 and the apex 19, which is indicated by a cross, can clearly be identified as being the structure with the highest activity in this example. The structure detection unit 7 detects therefore preferentially the heart muscle in the reconstructed intermediate images, followed by a detection of the apex.

The respiratory phase determination apparatus 1 further comprises a respiratory motion determination unit 10 for determining the respiratory motion of the living being based on the structure detected in the reconstructed intermediate images. In particular, the respiratory motion determination unit 10 is adapted to determine the positions of the structure in the reconstructed intermediate images as the respiratory motion of the structure and to determine for each reconstructed intermediate image the respective respiratory phase of the person 3 depending on the positions of the structure detected in the reconstructed intermediate images. For example, the respiratory phase determination apparatus 1 can comprise a respiratory phase image set providing unit 8 for providing a respiratory phase image set of the heart, wherein the respiratory phase image set comprises for different respiratory phases different images of the heart and wherein the respiratory motion determination unit 10 is adapted to determine the respiratory phase of a reconstructed intermediate image by comparing the position of the structure in the reconstructed intermediate image with the position of the structure in the respiratory phase image set. In this example, the respiratory motion determination unit 10 is adapted to determine the respiratory phase of a reconstructed intermediate image by determining the image of the provided respiratory phase image set showing the structure with the smallest distance to the structure shown in the reconstructed intermediate image and by determining the respiratory phase of the determined image of the respiratory phase image set with the smallest distance as the respiratory phase of the reconstructed intermediate image. The respiratory phase image set can be a multi-phase CT image or a multi-phase MR image set, wherein the respiratory phase image set comprises several CT or MR images for different respiratory phases and wherein a respiratory phase is determined for an intermediate PET image by determining the CT or MR image showing the apex position with the shortest distance to the apex position shown in the respective intermediate PET image. The respiratory phase of the respective CT or MR image with the shortest distance is then determined as the respiratory phase of the respective intermediate PET image. The respiratory phase image set can also be a multi-phase attenuation image set, which may be based on a multi-phase MR image set or a multi-phase CT image set or which may directly be a multi-phase CT image set. The multi-phase attenuation image set comprises for different respiratory phases different attenuation images, wherein different regions of the attenuation images representing different elements of the living being, in particular, different tissue types, comprise different corresponding attenuation values.

The respiratory cycle is divided into a certain number of respiratory segments, wherein each respiratory segment defines a respiratory phase. In particular, ten respiratory phases can be defined by dividing the respiratory cycle into ten respiratory segments. The reconstruction unit 6 is preferentially adapted to reconstruct for each of the respiratory phases, i.e. for each of the respiratory segments, a respiratory phase image based on the raw data of the respective respiratory phase. The reconstruction unit 6 can be adapted to use directly the raw data of the respective respiratory phase for generating a respiratory phase image being, in this embodiment, a respiratory phase NAC PET image, or the reconstruction unit 6 can be adapted to average the reconstructed intermediate NAC PET images of a same respective respiratory phase for producing for the respective respiratory phase a respiratory phase NAC PET image.

In an embodiment, the respiratory phase image set providing unit 8 is adapted to provide attenuation images of the living being for different respiratory phases bases on, for example, corresponding multi-phase CT or MR images, and the reconstructing unit 6 is adapted to attenuation-correct the different respiratory phase PET images based on the determined respiratory phases and the corresponding attenuation images of the living being. Moreover, the reconstruction unit 6 is preferentially adapted to register the different attenuation-corrected respiratory phase PET images and to average the registered respiratory phase PET images for producing a static image. Thus, the attenuation-corrected respiratory phase PET images can be aligned by a rigid, affine or elastic registration, or by any other suitable registration method, and the aligned respiratory phase PET images can be averaged for producing a "freezed" NAC PET image which is compensated for respiratory motion. The reconstruction unit can also be adapted to firstly register the NAC respiratory phase PET images and to average the NAC respiratory phase PET images for producing a static NAC PET image, wherein then the NAC respiratory phase PET image can be corrected by using a corresponding attenuation image. For example, the respiratory motion determination apparatus 1 can comprise an attenuation image providing unit 12 for providing a static attenuation image of the living being, wherein the reconstruction unit 6 can be adapted to attenuation correct the static NAC PET image based on the provided static attenuation image.

The raw data grouping unit 5, the reconstruction unit 6, the structure detection unit 7, the respiratory phase image set providing unit 8, the respiratory motion model providing unit 9, the respiratory motion determination unit 10 and the static attenuation image providing unit 12 can be regarded as being part of a processing device 20, which may be a computer, for processing the raw data.

The one or several reconstructed images can be shown on a display 13.

At least the final reconstructed images show preferentially not only the structure of the heart, but also at least one object of interest like a tumor to be investigated. The provided raw data are therefore preferentially not only indicative of the structure of the heart, but also of an object of interest which is influenced by respiratory motion. The structure of the heart is used for determining the respiratory motion, wherein the determined respiratory motion is then used for reconstructing an image of the object of interest using the determined respiratory motion.

The respiratory motion determination apparatus 1 can further be adapted to determine the respiratory phases of the living being based on the structure detected in the reconstructed intermediate images in another way. For example, the respiratory motion determination apparatus can further comprise a respiratory motion model providing unit 9 for providing a respiratory motion model of the living being, wherein the respiratory motion model provides for different respiratory phases different positions of the structure of the heart and wherein the respiratory motion determination unit 10 is adapted to determine the respiratory phase of a reconstructed intermediate image by comparing the position of the structure in the reconstructed intermediate image with the position of the structure in the respiratory motion model. In particular, the apex position of the heart muscle is mapped to the respiratory motion model for determining for each reconstructed intermediate image a respective respiratory phase. The attenuation image providing unit 12 can then provide a static attenuation image of the living being, which can be deformed by the reconstruction unit 6 in accordance with the provided respiratory motion model for producing different attenuation images for different respiratory phases. The attenuation image comprises for different elements of the living being like different kinds of tissue different attenuation values, wherein the reconstruction unit 6 can be adapted to attenuation-correct each reconstructed intermediate image based on the attenuation image produced for the respiratory phase of the respective reconstructed intermediate image by the above mentioned deformation of the static attenuation image. Also these attenuation-corrected intermediate images can be averaged for producing respiratory phase images, wherein a respiratory phase image is the average of the attenuation-corrected intermediate images assigned to the same respective respiratory phase. Optionally, the resulting attenuation-corrected respiratory phase images, in particular, the AC respiratory phase PET images, can be registered and averaged for producing a static image which is compensated for respiratory motion. In an alternative to attenuation-correcting the individual intermediate images, the produced respiratory phase images or the optional static image can be attenuation-corrected. Moreover, instead of determining a respiratory phase image by averaging the intermediate images, which correspond to the same respective respiratory phase, a respiratory phase image can be reconstructed by directly using the raw data, which correspond to the intermediate images of the respective same respiratory phase.

The respiratory motion determination apparatus can be adapted to allow determining the respiratory phases of the living being in a further other way. In particular, the detected structure of the heart in the different reconstructed intermediate images defines a movement of the structure, wherein the respiratory motion determination unit 10 can be adapted to fit a trajectory to the movement of the structure and to determine the respiratory phases based on the fitted trajectory, thereby defining respiratory phases for the reconstructed intermediate images. In this embodiment, the apex positions of the heart muscle from all reconstructed intermediate PET images are collected and the trajectory is fitted to a superposition or overlay of all apex positions shown in the different reconstructed intermediate PET images. The fitted trajectory describes, for example, a back and forth movement of the apex position along a line or an ellipse. The respiratory phases are preferentially determined based on the fitted trajectory by subdividing the trajectory into a number of boxes or intervals. For example, the trajectory can be subdivided into ten boxes or intervals, in order to define ten respiratory phases. Since each of the reconstructed intermediate images comprises an apex position in one of the boxes or intervals, each reconstructed intermediate image is assigned to a respiratory phase by determining in which of the boxes or intervals the apex position of the respective intermediate image is located. For each of the respiratory phases a respiratory phase image, in this embodiment, a respiratory phase PET image, can then be determined by averaging the intermediate images assigned to the same respiratory phase or by directly using the underlying raw data for reconstructing a respiratory phase image for the respective respiratory phase. The respiratory phase images can then be aligned with respect to each other as described above by using, for example, a rigid, affine or elastic registration, wherein the aligned respiratory phase images can be averaged for determining a single static image which is compensated for respiratory motion. The static image can be attenuation corrected by using a single static attenuation map, which may be based on a CT or MR image, or the intermediate or respiratory phase images can be attenuation corrected, before generating the static image which is compensated for respiratory motion.

Figure 4:
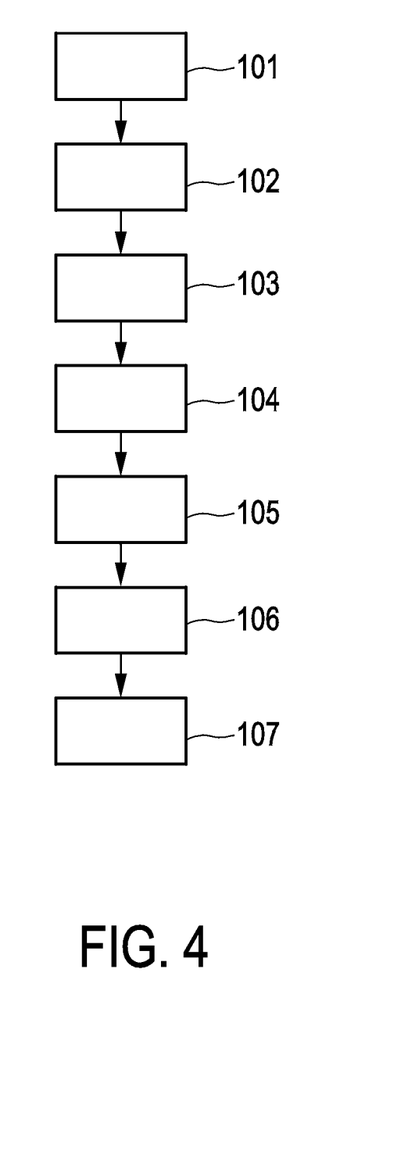
FIG. 4 shows a flowchart exemplarily illustrating an embodiment of a respiratory motion determination method for determining respiratory motion of a living being.

In the following an embodiment of a respiratory motion determination method will exemplarily be described with reference to a flowchart shown in FIG. 4.

In step 101, raw data are provided, which are assigned to different times, wherein the raw data are indicative of a structure of the heart of the living being and useable for reconstructing an image of the structure of the heart, wherein the structure of the heart is influenced by respiratory motion, by the raw data providing unit 2. In this embodiment, PET data are acquired by the PET data acquisition unit 2, wherein the PET data, i.e. the PET counts or events, are time stamped. Parallel to acquiring the raw data, the cardiac signal providing unit 11 provides a cardiac signal at the different times to which the raw data are assigned, wherein the cardiac signal is indicative of the heart cycles. In this embodiment, an ECG signal is acquired, while the PET data are acquired.

In step 102, the reconstruction unit 6 reconstructs intermediate images which show at least the structure being, in this embodiment, the apex of the heart muscle from the provided raw data. In particular, the raw data grouping unit 5 groups raw data of a same heart cycle in a group based on the provided cardiac signal and the reconstruction unit 6 reconstructs an intermediate image for each group depending on the raw data of the respective group.

In step 103, the structure detection unit 7 detects the structure in the reconstructed intermediate images, and in step 104 the respiratory phase determination unit 10 determines the positions of the structure in the reconstructed intermediate images as respiratory motion of the living being and determines the respiratory phases of the living being based on the positions of the structure detected in the reconstructed intermediate images. In particular, for each reconstructed intermediate image the respiratory phase of the living being is determined depending on the positions of the structure detected in the reconstructed intermediate images. For example, a respiratory phase can be determined for a reconstructed intermediate image by comparing the position of the structure in the reconstructed intermediate image with the position of the structure in a respiratory phase image set, which comprises for different respiratory phases different images of the living being showing the position of the structure in the respective respiratory phase. Moreover, the respiratory phase of a reconstructed intermediate image can be determined by comparing the position of the structure in the reconstructed intermediate image with the position of the structure in a respiratory motion model, wherein the respiratory motion model provides for different respiratory phases different positions of the structure. It is also possible to fit a trajectory to the movement of the structure detected in the intermediate images and to determine the respiratory phases based on the fitted trajectory as described above.

In step 105, the reconstruction unit 6 reconstructs for different respiratory phases different respiratory phase images based on the raw data of the respective respiratory phase. This reconstruction can be performed directly on the raw data of the respective phase or by averaging the reconstructed intermediate images of the same respective respiratory phase.

In step 106, the respiratory phase images are attenuation corrected by using, for example, a respiratory phase dependent attenuation image, i.e. different attenuation images for different respiratory phases, wherein an attenuation image comprises for different element of the living being, in particular, for different types of tissue, different attenuation values.

In step 107, the attenuation-corrected respiratory phase images can be registered and averaged to generate an attenuation-corrected static image which is compensated for respiratory motion.

The respiratory phase determination apparatus can be used for PET/CT imaging or PET/MR imaging. PET/CT imaging and PET/MR imaging have a tremendous impact on cancer management, because they do not only enable detection of tumors, but also allows for differential diagnoses. PET/CT imaging and PET/MR imaging can be used, for example, for the quantitative estimation of tumor response to therapy. Respiratory motion can generally limit the utility of PET/CT imaging and PET/MR imaging, on one hand due to blurring and on the other hand due to incorrect attenuation correction. Blurring can cause an overestimation of tumor volume and/or underestimation of tracer uptake. Incorrect attenuation correction can lead to an underestimation of tracer uptake, in particular, if the tumor is located close to an organ boundary with a distinctive change in attenuation, such as the lungs. An attenuation map, i.e. an attenuation image, for attenuation correction can be derived from a CT image, in particular, a low-resolution CT image, and its segmentation into different elements of the living being like air, fat, muscle, lungs et cetera. An MR image can also be segmented in a similar fashion and used for creating the attenuation map. The attenuation map can be a static attenuation map or it can be a multi-phase attenuation map, which may be based on a multi-phase CT or MR image, respectively. A multi-phase attenuation map offers a phase-matched attenuation correction such that in an ideal case each, for example, PET count, can be corrected for attenuation with respect to its underlying anatomy, and summed at a position consistent with the anatomy.

Current motion compensation techniques split the respiratory cycle into a predetermined, small number of, for example, ten respiratory phases by using an external gating device like a respiratory belt to track the respiratory phases and to create gated reconstructions within time windows, which correspond to the respiratory phases. Each of these reconstructed images then corresponds to an individual phase of the respiratory cycle, and can be overlaid correctly by using a respiratory model derived from, for example, a lung segmentation in a multi-phase CT or MR image. This gating relies on a stable correlation between the tracking signal and the respiratory state, which is very difficult to achieve even with visual feedback systems, in particular, audio-visual feedback systems, and even if the feedback systems are optimally placed. As a consequence, the final images reconstructed using phase-based gating typically contain counts/events also from non-corresponding phases, which induces severe image artifacts. The respiratory phase determination apparatus is therefore preferentially adapted to use respiration-induced heart motion as an anatomical image-based tracker for determining the respiratory phase. In particular in PET images the heart muscle is clearly visible and of much greater intensity then, for example, lung or liver structures. Since the heart resides directly on top of the diaphragm, its motion is a direct measure of the respiratory state. However, the respiration-induced motion of the heart is overlaid with its beating motion. Typically, an adults heart at rest beats 40 to 80 times per minute, thus a heart cycle is completed after about 1 second. A breathing cycle takes typically 10 to 15 seconds. Averaging the heart motion of one heart beat determines the mean respiratory state during the corresponding interval. This can be used to look up the correct anatomical phase both for the attenuation correction and for the anatomically consistent overlay of the reconstructed image.

Although in the above described embodiments the cardiac signal is an ECG signal, the cardiac signal can also be any other signal being indicative of the heart cycles. For example, a heart beat sensor attached to a person's wrist can be used, which measures the heart cycle depending on, for example, a pulse measurement.

Although in the above described embodiments the respiratory phases have been determined from PET images, in other embodiments the respiratory phase determination apparatus can be adapted to determine the respiratory phases from images generated by other imaging modalities like SPECT images, CT images, MR images, ultrasound images, et cetera.

Although in above described embodiments the motion of the structure detected in the reconstructed intermediate images has been determined as respiratory motion of the living being, wherein this motion has been used for determining respiratory phases, which are used for reconstructing an image of the living being, the respiratory motion determination apparatus can also be adapted to determine respiratory motion of the living being based on the structure detected in the intermediate images, without necessarily determining respiratory phases, wherein the determined respiratory motion together with the raw data can be used to reconstruct a respiratory motion compensated image. For example, a respiratory motion model can be provided, which describes the respiratory motion of an entire thorax region of the living being depending on the determined respiratory motion of the structure, in particular, depending on the respiratory motion of the apex of the heart muscle. The respiratory motion of the entire thorax portion together with the raw data can then be used for reconstructing a respiration compensated image of at least a part of the thorax. In an embodiment, raw data corresponding to the same position of the structure and, thus, to the same respiratory motion state, can be used for reconstructing motion state images, which can then be combined in accordance with the respiratory motion model for reconstructing a motion compensated image. In another embodiment, the raw data can be corrected for respiratory motion by using the determined respiratory motion of the entire thorax, wherein then the motion corrected raw data can be reconstructed for generating a respiratory motion compensated image. For instance, if the raw data are PET data, each corresponding line-of-response can be shifted in accordance with the determined respiratory motion of the entire thorax.

The respiratory phase determination apparatus and method can be adapted to be used in a PET system, in particular, a time of flight PET system, a PET/CT system, a PET/MR system et cetera, especially for tumor response assessment in the thorax, in particular, in the lungs.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations like the calculations performed for reconstructing images, determining phases of the reconstructed images and correcting the images with respect to attenuation, et cetera performed by one or several unit or devices can be performed by any other number of units or devices. For example, steps 101 to 107 can be performed by a single unit or by any other number of different units. The calculation and/or the control of the respiratory motion determination apparatus in accordance with the respiratory motion determination apparatus can be implemented as program codes means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a respiratory motion determination apparatus for determining respiratory motion of a living being. A raw data providing unit provides raw data assigned to different times, wherein the raw data are indicative of a structure like the apex of the heart muscle, which is influenced by cardiac motion and by respiratory motion, and a reconstruction unit reconstructs intermediate images of the structure from the provided raw data. A structure detection unit detects the structure in the reconstructed intermediate images, and a respiratory motion determination unit determines the respiratory motion of the living being based on the structure detected in the reconstructed intermediate images. This allows determining respiratory motion with high accuracy, without relying on, for example, a stable correlation between a tracking signal of an external respiratory gating device and respiratory phases.

The invention claimed is:

1. A respiratory motion determination apparatus for determining respiratory motion of a living being, the respiratory motion determination apparatus comprising:
    a raw data providing unit for providing raw data assigned to different times, wherein the raw data are indicative of a structure, which is influenced by cardiac motion and by respiratory motion of the living being and which is a structure of the living being, wherein the raw data are usable for reconstructing an image of the structure,
    a reconstruction unit for reconstructing intermediate images of the structure from the provided raw data,
    a structure detection unit for detecting the structure in the reconstructed intermediate images,
    a respiratory motion determination unit for determining the respiratory motion of the living being based on the structure detected in the reconstructed intermediate images, wherein the raw data providing unit is adapted to provide nuclear raw data as the raw data and the respiratory motion determination unit is adapted to determine the positions of the structure in the reconstructed intermediate images as the respiratory motion of the living being and to determine for each reconstructed intermediate image the respective respiratory phase of the living being depending on the positions of the structure detected in the reconstructed intermediate images.

2. The respiratory motion determination apparatus as defined in claim 1, further comprising:
    a cardiac signal providing unit for providing a cardiac signal at the different times to which the raw data are assigned, wherein the cardiac signal is indicative of heart cycles,
    a raw data grouping unit for grouping raw data of a same heart cycle in a group based on the provided cardiac signal,
    wherein the reconstruction unit is adapted to reconstruct an intermediate image for each group depending on the raw data of the respective group.

3. The respiratory motion determination apparatus as defined in claim 1, wherein the structure detection unit is adapted to detect the apex of the heart muscle as the structure.

4. The respiratory motion determination apparatus as defined in claim 1, further comprising:
a respiratory phase image set providing unit for providing a respiratory phase image set of the living being, wherein the respiratory phase image set comprises for different respiratory phases different images of the structure, wherein the respiratory motion determination unit is adapted to determine the respiratory phase of a reconstructed intermediate image by comparing the position of the structure in the reconstructed intermediate image with the position of the structure in the respiratory phase image set.

5. The respiratory motion determination apparatus as defined in claim 1, further comprising:
a respiratory motion model providing unit for providing a respiratory motion model of the living being, wherein the respiratory motion model provides for different respiratory phases different positions of the structure, wherein the respiratory motion determination unit is adapted to determine the respiratory phase of a reconstructed intermediate image by comparing the position of the structure in the reconstructed intermediate image with the position of the structure in the respiratory motion model.

6. The respiratory motion determination apparatus as defined in claim 1, wherein the respiratory motion determination unit is adapted to fit a trajectory to the respiratory movement of the structure and to determine respiratory phases based on the fitted trajectory, thereby defining respiratory phases for the reconstructed intermediate images.

7. The respiratory motion determination apparatus as defined in claim 1, wherein the reconstruction unit is adapted to reconstruct for different respiratory phases different respiratory phase images based on the raw data of the respective respiratory phase.

8. The respiratory motion determination apparatus as defined in claim 7, wherein the raw data are nuclear raw data and wherein the reconstructed intermediate images are reconstructed nuclear images, wherein the respiratory motion determination apparatus further comprises a respiratory phase image set providing unit for providing a respiratory phase image set of the living being, wherein the respiratory phase image set comprises for different respiratory phases different attenuation images of the living being, wherein the reconstruction unit is further adapted to attenuation-correct the different nuclear respiratory phase images based on the determined respiratory phases and the provided respiratory phase image set.

9. A respiratory motion determination apparatus for determining respiratory motion of a living being, the respiratory motion determination apparatus comprising:
a raw data providing unit for providing raw nuclear data assigned to different times, wherein the raw nuclear data are indicative of a structure, which is influenced by cardiac motion and by respiratory motion of the living being and which is a structure of the living being, wherein the raw data are usable for reconstructing an image of the structure;
a reconstruction unit for reconstructing intermediate nuclear images of the structure from the provided raw data;
a structure detection unit for detecting the structure in the reconstructed intermediate images;
a respiratory motion determination unit for determining the respiratory motion of the living being based on the structure detected in the reconstructed intermediate images;
wherein the respiratory motion determination apparatus further comprises:
a respiratory motion model providing unit for providing a respiratory motion model of the living being, wherein the respiratory motion model provides for different respiratory phases different positions of the structure, and
a static attenuation image providing unit for providing a static attenuation image,
wherein the reconstruction unit is adapted to:
deform the static attenuation image in accordance with the provided respiratory motion model for producing different attenuation images for different respiratory phases,
attenuation-correct each reconstructed intermediate image based on the attenuation image produced for the respiratory phase of the respective reconstructed intermediate nuclear image.

10. The respiratory motion determination apparatus as defined in claim 1, wherein the reconstruction unit is adapted to register the different respiratory phase images and to average the registered respiratory phase images for producing a static image.

11. The respiratory motion determination apparatus as defined in claim 1, wherein the reconstruction unit is adapted to reconstruct a respiratory motion compensated image from the raw data and the determined respiratory motion.

12. A respiratory motion determination method for determining respiratory motion of a living being, the respiratory motion determination method comprising:
providing nuclear raw data assigned to different times from a nuclear imaging system, wherein the raw nuclear data are indicative of a structure of the living being, which is influenced by cardiac motion and by respiratory motion of the living being and which is a structure of the living being, wherein the nuclear raw data are usable for reconstructing an image of the structure,
reconstructing non-attenuation corrected intermediate nuclear images of the structure from the provided nuclear raw data with a computer system,
detecting positions in the structure in the reconstructed non-attenuated corrected intermediate nuclear images, with the computer system,
determining a respiratory phase of the living being in each reconstructed intermediate nuclear image based on the positions of the structure detected in the reconstructed intermediate nuclear images, with the computer system.

13. A non-transitory computer-readable medium carrying program code for controlling a computer to carry out the steps as defined in claim 12, to determine the respiratory motion of the living being.

14. A respiratory motion determining apparatus for determining respiratory motion of a living being based on nuclear data, the respiratory motion determining apparatus comprising:
a computer system configured to:
receive raw nuclear data over a plurality of times, the raw nuclear data being indicative of a portion of the living being including a structure which is influenced by cardiac motion and respiratory motion;
reconstruct the raw nuclear data into a plurality of intermediate nuclear images corresponding to the plurality of times;

determine locations of the structure in the plurality of intermediate nuclear images;

based on the determined locations, determining respiratory phases of the living being in the intermediate nuclear images.

15. The respiratory motion determining apparatus as defined in claim 14, wherein the computer system is further configured to:

deform a static attenuation image into the respiration phase of each intermediate nuclear image; and attenuation correct each reconstructed intermediate image based on the deformed static attenuation image.

16. The respiratory motion determining apparatus as defined in claim 14, further including:

a cardiac monitor configured to monitor a cardiac cycle of the living being and generate a cardiac signal; and wherein the computer system is configured to group the raw nuclear data based on the cardiac cycle signal and the respiratory phase.

17. The respiratory motion determining apparatus as defined in claim 14, wherein the structure is an apex of a heart of the living being.

18. The respiratory motion determination method as defined in claim 12, further including, with the computer system:

from the determined respiratory phases, generating a motion model;

based on the motion model, deforming a static attenuation image corresponding to each respiratory phase;

attenuation correcting each of the reconstructed non-attenuation corrected intermediate nuclear images.

* * * * *